United States Patent
Frayling et al.

(10) Patent No.: US 10,690,689 B2
(45) Date of Patent: Jun. 23, 2020

(54) MICROFLUIDIC DEVICE FOR CHARACTERZING POLYNUCLEOTIDES

(71) Applicants: BASE4 INNOVATION LTD, Cambridge, Cambridgeshire (GB); UNITED KINGDOM RESEARCH AND INNOVATION, Swindon (GB)

(72) Inventors: Cameron Alexander Frayling, Cambridgeshire (GB); Barnaby Balmforth, Cambridgeshire (GB); Bruno Flavio Nogueira de Sousa Soares, Cambridgeshire (GB); Thomas Henry Isaac, Cambridgeshire (GB); Boris Breiner, Cambridgeshire (GB); Alessandra Natale, Cambridgeshire (GB); Michele Amasio, Cambridgeshire (GB); Paul Dear, Wiltshire (GB)

(73) Assignees: BASE4 INNOVATION LTD, Cambridge, Cambridgeshire (GB); UNITED KINGDOM RESEARCH AND INNOVATION, Swindon (GB)

( * ) Notice: Subject to any disclaimer, the term of this patent is extended or adjusted under 35 U.S.C. 154(b) by 54 days.

(21) Appl. No.: 15/725,646

(22) Filed: Oct. 5, 2017

(65) Prior Publication Data
US 2018/0044729 A1 Feb. 15, 2018

Related U.S. Application Data

(62) Division of application No. 14/782,654, filed as application No. PCT/GB2014/051105 on Apr. 9, 2014, now Pat. No. 9,828,631.

(30) Foreign Application Priority Data

Apr. 9, 2013 (GB) .................................. 1306444.9

(51) Int. Cl.
| | | |
|---|---|---|
| G01N 35/08 | (2006.01) | |
| C12Q 1/6869 | (2018.01) | |
| B01L 3/00 | (2006.01) | |

(52) U.S. Cl.
CPC ........... G01N 35/08 (2013.01); C12Q 1/6869 (2013.01); B01L 3/502784 (2013.01)

(58) Field of Classification Search
CPC ............ C12Q 1/6869; C12Q 2565/629; C12Q 2563/159; C12Q 2565/301; B01L 3/502784; B01L 3/0241; G01N 35/08
See application file for complete search history.

(56) References Cited

U.S. PATENT DOCUMENTS

| 5,528,046 A | 6/1996 | Ishikawa |
|---|---|---|
| 5,674,743 A | 10/1997 | Ulmer |

(Continued)

FOREIGN PATENT DOCUMENTS

| JP | 6-148076 | 5/1994 |
|---|---|---|
| WO | 94/18218 | 8/1994 |

(Continued)

OTHER PUBLICATIONS

International Search Report dated Jul. 22, 2014 in International (PCT) Application No. PCT/GB2014/051105.

(Continued)

*Primary Examiner* — Joseph G. Dauner
(74) *Attorney, Agent, or Firm* — Wenderoth, Lind & Ponack, L.L.P.

(57) ABSTRACT

A microfluidic sequencing device in which a stream of microdroplets at least some of which contain a single nucleotide base are made to undergo reaction with a capture system to capture and detect an ordered sequence of single (Continued)

nucleotide bases generated by progressive pyrophosphorolysis.

8 Claims, 3 Drawing Sheets

Specification includes a Sequence Listing.

(56) References Cited

U.S. PATENT DOCUMENTS

| | | |
|---|---|---|
| 6,268,146 B1 | 7/2001 | Shultz et al. |
| 2003/0138831 A1 | 7/2003 | Kwagh et al. |
| 2003/0187237 A1 | 10/2003 | Chan et al. |
| 2008/0003142 A1* | 1/2008 | Link .................. B01F 3/0807 422/82.08 |
| 2009/0280475 A1 | 11/2009 | Pollack et al. |
| 2010/0184020 A1 | 7/2010 | Beer |

FOREIGN PATENT DOCUMENTS

| | | |
|---|---|---|
| WO | 03/046216 | 6/2003 |
| WO | 03/080861 | 10/2003 |
| WO | 2004/002627 | 1/2004 |
| WO | 2006/115570 | 11/2006 |
| WO | 2008/092150 | 7/2008 |
| WO | 2009/085215 | 7/2009 |
| WO | 2010/077859 | 7/2010 |
| WO | 2013/037962 | 3/2013 |

OTHER PUBLICATIONS

Nutiu et al., "Structure-Switching Signaling Aptamers: Transducing Molecular Recognition into Fluorescence Signaling", Chem. European Journal, vol. 10, No. 8, 2004, pp. 1868-1876.

Bayley, "Sequencing single molecules of DNA", Current Opinion in Chemical Biology, vol. 10, 2005, pp. 628-637.

Stephan et al., "Towards a general procedure for sequencing single DNA molecules", Journal of Biotechnology, vol. 86, 2001, pp. 255-267.

Boles et al., "Droplet-Based Pyrosequencing Using Digital Microfluidics", Analytical Chemistry, vol. 83, 2011, pp. 8439-8447.

Theberge et al., "Microdroplets in Microfluidics: An Evolving Platform for Discoveries in Chemistry and Biology", Angewandte Chem. Int. Ed., vol. 49, 2010, pp. 5846-5868.

Eicher et al., "Microfluidic devices for diagnostic applications", Expert Review of Molecular Diagnostics, vol. 11, No. 5, XP009168535, 2011, pp. 505-519.

Tan et al., "Monodispersed microfluidic droplet generation by shear focusing microfluidic device", Sensors and Actuators B, 2005, vol. 114, pp. 350-356.

Extract from Medical Molecular Cell Biology in Chinese, 2005, ISBN 7-309-04634-X, with English translation, 3 pages.

* cited by examiner

MICROFLUIDIC DEVICE FOR CHARACTERZING POLYNUCLEOTIDES

This invention relates to a method for characterising polynucleotides such as those derived from naturally occurring RNA or DNA by capturing and detecting an ordered sequence of single nucleotide bases generated therefrom by progressive pyrophosphorolysis.

Next generation sequencing of genetic material is already making a significant impact on the biological sciences in general and medicine in particular as the unit cost of sequencing falls in line with the coming to market of faster and faster sequencing machines. Thus, in one such machine, a double-stranded DNA analyte is first broken down into a plurality of smaller polynucleotide fragments each of which is first adenylated on both ends of one strand so that a single-stranded first oligonucleotide can be bound to both ends of its compliment by hybridisation to the unpaired adenine base. The treated fragments so obtained are then size-selected and captured on a surface coated with bound single-stranded second oligonucleotides which themselves are the sequence compliment of the first so that in effect a library of surface-bound double-stranded fragments can be created by further hybridisation. In a subsequent clustering step, these library components are then clonally amplified millions of times on the surface using extension and isothermal bridging reactions to utilise unused second oligonucleotides. This, in effect, creates a dense concentration of the polynucleotide fragment bound to the surface through one of its strands. The unbound complimentary strand of each fragment is then removed to leave bound single-stranded fragments ready for sequencing. In the sequencing stage, each of these single-stranded fragments is primed and its complimentary strand recreated by extension using the polymerase chain reaction and a mixture of the four characteristic nucleotide bases of DNA in dideoxynucleotide triphosphate (ddNTP) form. Each ddNTP type is end-blocked with a moiety which is labelled with a different fluorophore fluorescing at a different wavelength. The extension reaction then takes the form of a cycle of three steps; first the relevant ddNTP is incorporated into to the growing strand; secondly the nucleotide base it contains is identified by illuminating the sample and detecting the wavelength of the fluorescence and finally the end block and its associated fluorophore are removed to allow the next extension event to occur. By this means, the sequence of the complimentary strand can be built up base-by-base. It will be appreciated that, whilst this approach can be highly automated and can generate sequence reads of high accuracy, its speed of operation is limited by the rate of the extension cycle. Thus, in practice, use of the technology tends to involve parallel processing of relatively short polynucleotide fragments and assembly of the whole sequence from the various reads obtained therefrom. This in itself can lead to computational complexities and the potential introduction of errors.

More recently efforts have been made to develop direct sequencing methods. For example, WO 2009/030953 discloses a new fast sequencer in which inter alia the sequence of nucleotide bases or base pairs in a single- or double-stranded polynucleotide sample (e.g. naturally occurring RNA or DNA) is read by translocating the same through a nano-perforated substrate provided with plasmonic nanostructures juxtaposed within or adjacent the outlet of the nanopores. In this device, the plasmonic nanostructures define detection windows (essentially an electromagnetic field) within which each nucleotide base (optionally labelled) is in turn induced to fluoresce or Raman scatter photons in a characteristic way by interaction with incident light. The photons so generated are then detected remotely, multiplexed and converted into a data stream whose information content is characteristic of the nucleotide base sequence associated with the polynucleotide. This sequence can then be recovered from the data stream using computational algorithms embodied in corresponding software programmed into a microprocessor integral therewith or in an ancillary computing device attached thereto. Further background on the use of plasmonic nanostructures and their associated resonance characteristics can be found in for example Adv. Mat. 2004, 16(19) pp. 1685-1706.

Another apparatus for fast sequencing polynucleotides is described, for example, in U.S. Pat. Nos. 6,627,067, 6,267,872 and 6,746,594. In its simplest form, this device employs electrodes, instead of plasmonic nanostructures, to define the detection window across the substrate or in or around the outlet of the nanopore. A potential difference is then applied across the electrodes and changes in the electrical characteristics of the ionic medium flowing therebetween, as a consequence of the electrophoretic translocation of the polynucleotide and associated electrolyte through the nanopore, is measured as a function of time. In this device, as the various individual nucleotide bases pass through the detection window they continuously block and unblock it causing 'events' which give rise to characteristic fluctuations in current flow or resistivity. These fluctuations are then used to generate a suitable data stream for analysis as described above.

The generation of stable droplet streams, especially microdroplet streams, is another developing area of technology that already has applications in molecular biology. For example, U.S. Pat. No. 7,708,949 discloses a novel microfluidic method for generating stable water droplets in oil whilst for example US2011/0250597 describes utilisation of this technology to generate microdroplets containing a nucleic acid template (typically a polynucleotide DNA or RNA fragment) and a plurality of primer pairs that enable the template to be amplified using the polymerase chain reaction. Other patent applications relating to the field generally include JP2004/290977, JP2004/351417, US2012/0122714, US2011/0000560, US2010/01376163, US2010/0022414 and US2008/0003142.

WO 2004/002627 discloses a method for creating liquid-liquid and gas-liquid dispersions using various devices comprising creating a discontinuous section between upstream and downstream microfluidic regions. However its application to single nucleotide DNA sequencing is not taught.

WO 2010/077859 teaches a droplet actuator comprising a substrate provided with electrodes, a reactor path and nucleotide base, wash-buffer, sample and enzyme reservoirs. Whist the actuator is generically said to be useful for the amplification and sequencing of nucleic acids, there is no teaching of the analyte degradation method we describe below. Rather, it is concerned with a completely different approach; observing the synthesis of a complimentary strand of the analyte using pyrosequencing. US 2009/0280475 is concerned with similar subject-matter.

Biological probes, which typically comprise single-stranded oligonucleotides of known sequence order less than 1000 nucleotides long, are widely used in analytical molecular biology. Such probes typically work by attaching themselves to the target (for example one derived from the DNA of a naturally-occurring pathogen) when sufficient sequence complimentarity exists between the nucleotide bases of the probe and the target. Typically the nucleotides of such probes are labelled with detectable elements such as radioactive or fluorescent markers so that when the probe is used to treat an analyte solution or substrate in or on which the target is thought to have been captured, the presence or absence of the target is revealed by searching for and detecting the detection element's characteristic detection property.

One class of such probes is represented by materials known in the art as 'molecular beacons' as for example described in U.S. Pat. No. 8,211,644. These probes are comprised of single-stranded oligonucleotides which have been in effect folded back onto themselves to create a residual single-stranded loop which acts as the probe's sensor and a short stem where the nucleotides adjacent the two ends are bound to each other through complimentary nucleotide base pairing; thereby creating a double-stranded region. This arrangement, which can be likened to a hairpin in which the single-stranded loop is attached to complimentary strands of the same end of a notional double-stranded oligonucleotide, is highly strained. To the free 3' and 5' ends of the oligonucleotide (now adjacent to one another and at the remote end of the stem) are respectively attached a fluorophore and a quencher. Their geometric proximity to each other then ensures that no significant fluorescence occurs. In use, the target binds to the single-stranded loop causing additional strain so that when the probe is heated the stem unzips causing distancing of the fluorophore and quencher and allowing the former to fluoresce.

We have now developed a new sequencing method which in one embodiment involves generating a stream of nucleotide bases whose ordering is characteristic of the sequence in the analyte by progressive degradation of the analyte; and a subsequent capture of each nucleotide base in a way which enables it to be detected.

WO 94/18218 discloses a genome sequencer in which an ordered stream of single nucleotides is separated from an analyte and thereafter contained in a fluorescent-enhancing solid matrix where each nucleotide is excited using a laser and its characteristic spectroscopic emission detected. The single nucleotide transfer method used by this sequencer involves creating a single dual-sheath of flowing immiscible liquids rather than a series of droplets. Furthermore, the sequencer described seeks to detect the single nucleotides directly rather than employing a capture system and fluorophore release method of the type we describe. We believe that this is a drawback as it will lead to signal-to-noise ratio problems when the emission come to be detected. This will compromise the overall sensitivity and therefore practical applicability of the sequencer itself.

Stephan et al Journal of Biotechnology 86 (2001) pp. 255-267 teaches a general method for counting single nucleotides generated by exonucleolytic degradation of an immobilised DNA sample labelled with fluorophores. However no information is provided about differentiating between the different single nucleotide types generated.

The use of the progressive exonucleolytic degradation of polynucleotides to generate a stream of single nucleotide bases has been disclosed in schematic form at mrc-lmb.cam.ac.uk/happy/HappyGroup/seq.html although little information about the actual methodology employed is provided. Furthermore, WO 03/080861 describes a sequencing method in which a DNA analyte is sequentially degraded to an ordered stream of single nucleotides by means of pyrophosphorolysis carried out in the presence of a pyrophosphate anion labelled with an intelligent dye. In one example the pyrophosphate anion is labelled with the dye JF-4 which has differing fluorescent lifetimes depending on the particular nucleotide type to which it is attached. The stream of labelled single nucleotides is then excited by a laser and analysed spectroscopically to determine the nature and therefore the ordering of the nucleotides. Once again the single nucleotides are detected directly rather than by employing the capture system and fluorophore release method we describe below. It is believed therefore that this method will also lead to signal-to-noise ratio and therefore sensitivity problems.

According to the present invention there is therefore provided a method for determining the sequence of nucleotide bases in a polynucleotide analyte characterised by the steps of (1) generating a stream of single nucleotide bases from the analyte by pyrophosphorolysis; (2) producing captured molecules by reacting each single nucleotide base with a capture system labelled with detectable elements in an undetectable state; (3) releasing the detectable elements from each captured molecule in a detectable state and (4) detecting the detectable elements so released and determining the sequence of nucleotide bases therefrom.

DETAILED DESCRIPTION OF THE INVENTION

Figure 1:
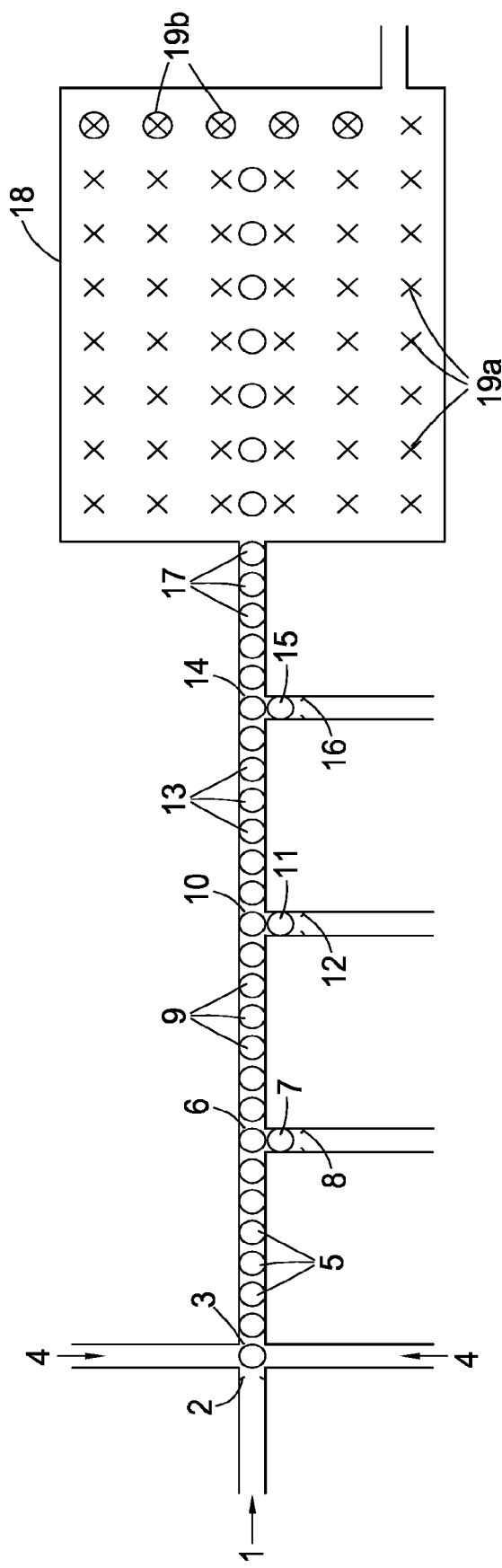
FIG. 1 illustrates a microfluidic sequencing device in which a stream of microdroplets at least some of which contain a single nucleotide base are made to undergo reaction with a capture system of the first class described above.

As set forth above, described herein is a method for determining the sequence of nucleotide bases in a polynucleotide analyte characterised by the steps of (1) generating a stream of single nucleotide bases from the analyte by pyrophosphorolysis; (2) producing captured molecules by reacting each single nucleotide base with a capture system labelled with detectable elements in an undetectable state; (3) releasing the detectable elements from each captured molecule in a detectable state and (4) detecting the detectable elements so released and determining the sequence of nucleotide bases therefrom.

Step (1) of the method of the present invention comprises generating a stream of single nucleotide bases from the polynucleotide analyte by pyrophosphorolysis. The analyte employed in this step is suitably a double-stranded polynucleotide comprised of many nucleotide bases. In principal the length of the polynucleotide can be unlimited including up to the many millions of nucleotide bases found in a human genome fragment. The analyte itself is suitably RNA or DNA of natural origin although the method can also be used to sequence synthetically produced RNA or DNA or other nucleic acids made up wholly or in part of nucleotide bases that are not commonly encountered in nature; i.e. nucleotide bases other than adenine, thymine, guanine, cytosine and uracil. Examples of these include 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine.

In one embodiment of the invention, step (1) comprises a first sub-step of attaching the polynucleotide analyte to a substrate. Typically, the substrate comprises a microfluidic surface, a micro-bead or a permeable membrane made out of glass or a non-degradable polymer. Preferably, the substrate further comprises a surface adapted to receive the analyte. There are many ways in which the analyte can be attached to such surfaces all of which can in principle be used. For example, one method involves priming a glass surface with a functionalised silane such as an epoxysilane, an aminohydrocarbylsilane or a mercaptosilane. The reactive sites so generated can then be treated with a derivative of the analyte which has a terminal amine, succinyl or thiol group.

It is a preferable feature of step (1) that the analyte is pyrophosphorolysed to generate a stream of single nucleotide bases whose ordering corresponds to that of the analyte. This step is preferably carried out at a temperature in the range 20 to 90° C. in the presence of a reaction medium comprising an enzyme. Preferably it is carried out under conditions of non-equilibrium flow so that the single nucleotide bases are continually removed from the reaction zone. Most preferably, the reaction is carried out by causing an aqueous buffered medium containing the enzyme and the other typical additives to continuously flow over the surface to which the analyte is bound.

In one preferred embodiment, the enzyme used is one which can cause progressive 3'-5' pyrophosphorolytic degradation of the analyte to yield deoxyribonucleotide triphosphates with high fidelity and at a reasonable reaction rate. Preferably this degradation rate is as fast as possible and in one embodiment lies in the range 1 to 50, preferably 1 to 20 nucleotide bases per second. Further information about the pyrophosphorolysis reaction as applied to the degradation of polynucleotides can be found for example in J. Biol. Chem. 244 (1969) pp. 3019-3028. The enzyme which is preferably employed in this pyrophosphorolysis reaction is suitably selected from the group consisting of those polymerases which show essentially neither exo- nor endonuclease activity under the reaction conditions. Examples of polymerases which can be advantageously used include, but are not limited to, the prokaryotic pol 1 enzymes or enzyme derivatives obtained from bacteria such as *Escherichia coli* (e.g. Klenow fragment polymerase), *Thermus aquaticus* (e.g. Taq Pol) and *Bacillus stearothermophilus, Bacillus caldovelox* and *Bacillus caldotenax*. Suitably, the pyrophosphorolytic degradation is carried out in the presence of a medium which further comprises pyrophosphate anion and magnesium cations; preferably in millimolar concentrations.

In step (2) of the method of the present invention each single nucleotide base generated in step (1) is captured by a capture system itself comprising an oligomer of nucleotide bases. Preferably, before this step is carried out the aqueous medium containing the single nucleotide bases is treated with a pyrophosphatase to hydrolyse any residual pyrophosphate to phosphate anion. In a first embodiment, the capture system comprises one of a class of pairs of first and second oligonucleotides. The first oligonucleotide in such a pair preferably comprises (a) a first double-stranded region and (b) a second single-stranded region comprised of n nucleotide bases wherein n is greater than 1 preferably greater than 5. In one sub-class, the first oligonucleotide can be regarded as having a molecular structure derived from a notional or actual single-stranded oligonucleotide precursor where the double-stranded region has been created by partially folding the 3' end of the precursor back on itself to generate a configuration which can be termed 'j shaped'. In another sub-class, the first oligonucleotide is generated by hybridising a third, shorter single-stranded oligonucleotide onto the 3' end of a longer fourth single-stranded oligonucleotide and then rendering the end of the resulting molecule which is double-stranded 'blunt' by means of a protecting group which for example bridges the final nucleotides of the two strands. Typically, the total length of the first oligonucleotide is up to 150 nucleotide bases, preferably between 20 and 100 nucleotide bases. At the same time it is preferred that the integer n is between 5 and 40, preferably between 10 and 30.

As regards the second oligonucleotide in the pair, this is single-stranded and suitably has a nucleotide base sequence which is wholly or partially the compliment of that of the single-stranded region of the first oligonucleotide starting one nucleotide base beyond the end of the double-stranded region. The length of the second oligonucleotide is not critical and can be longer or shorter than the single-stranded region to which it can bind although it is preferably not n–1 nucleotide bases long. More preferably, the length of the second oligonucleotide is chosen so that in the captured molecule a short overhang of unpaired nucleotide bases (e.g. 2 to 10 nucleotide bases) remains on one or other of the two strands thereof. Preferably, in this class the detectable elements are located on the second oligonucleotide. Capture systems of this class work by attaching the single nucleotide base to the double-stranded end of the first oligonucleotide and hybridising the second oligonucleotide onto the remaining single-stranded region to generate a captured molecule which is double-stranded apart from its overhang.

In a second embodiment, the capture system comprises a class of single oligonucleotides each consisting of a single-stranded nucleotide region the ends of which are attached to two different double-stranded regions. In the capture systems of this class, the single-stranded nucleotide region is comprised of one nucleotide base only making the probe extremely selective for the detection of the target i.e. the complimentary single nucleotide base in the droplet stream.

Turning to the double-stranded oligonucleotide region(s), it is preferred that they are derived or derivable from two oligonucleotide precursors, each preferably closed looped, or from a common single-stranded oligonucleotide precursor by folding the latter's ends back on themselves to create two closed-loop oligonucleotide base regions with an intermediate gap constituting the single-stranded nucleotide region. In all cases the effect is the same; adjacent to the ends of the single-stranded nucleotide region will be 3' and 5' free ends on the other strand of the oligonucleotide region to which the corresponding 5' and 3' ends of the target can be attached. Thus use of the capture system involves a process of attaching the single-stranded nucleotide region to the target single nucleotide base by joining up the available 3' and 5' ends of the capture system to generate a captured molecule which is double-stranded along its whole length.

Suitably, the double-stranded oligonucleotide region(s) are up to 50 nucleotide base pairs long, preferably up to 45 nucleotide base pairs, more preferably in the range 5 to 40 nucleotide base pairs and most preferably in the range 10 to 30. Longer regions may be used but the potential risk that access to the single-stranded nucleotide region by the target may become restricted through entanglement. This makes this embodiment potentially less attractive.

In this class it is preferred that the detectable elements bound to the double-stranded oligonucleotide region(s) are located remote from the single-stranded nucleotide region. Finally in one embodiment it is preferred that at least one of the double-stranded oligonucleotide regions comprises at least one restriction enzyme recognition site preferably adjacent the region where the detectable elements are located or clustered. For these capture systems, liberation of the fluorophores comes about by first a restriction enzyme exhibiting endonucleolytic behaviour and making a double-stranded cut in the captured molecule at the site mentioned above. The short fragments so created may then be degraded further by an exonuclease into single nucleotides at least some of which will be labelled with fluorophores. Thus, when the captured molecule comprises multiple fluorophores this leads to the release of a cascade of fluorophores which, by virtue of them now being separated from each other and/or their associated quenchers, are now free to fluoresce in the normal way. Such a restriction enzyme recognition site will typically comprise a specific sequence of from 2 to 8 nucleotide pairs. In another preferred embodiment the restriction enzyme recognition site will be one created by binding of the single nucleotide to the single-stranded nucleotide region.

For both of the classes mentioned above, it is preferred to employ a mixture of at least two different sets of capture molecules each selective for a different complimentary nucleotide base and each employing a different detectable element. These may be from the same or different classes. In a preferred embodiment, each set of capture molecules will have different associated detectable elements so that, when the corresponding detection property is eventually detected, the nucleotide base can be uniquely identified. For example, when the analyte is DNA or RNA it is most preferable to employ four different capture systems with each one being selective for a different nucleotide base characteristic of these molecules.

It is a further feature of all the capture systems of the present invention, that they are labelled with multiple detectable elements which are substantially undetectable when the capture system is in an unused state. Suitably these detectable elements are ones which are adapted to be detected by an optical event. In one preferred embodiment, the detectable elements comprise fluorophores and each unused capture system is essentially non-fluorescing at those wavelengths where the fluorophores are designed to be detected. Thus, although a fluorophore may exhibit general, low-level background fluorescence across a wide part of the electromagnetic spectrum, there will typically be one or a small number of specific wavelengths or wavelength envelopes where the intensity of the fluorescence is at a maximum. It is at one or more of these maxima where the fluorophore is characteristically detected that essentially no fluorescence should occur. In the context of this patent, by the term 'essentially non-fluorescing' or equivalent wording is meant that the intensity of fluorescence of the total number of fluorophores attached to the second oligonucleotide at the relevant characteristic wavelength or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the unused state of the capture system the fluorophores are essentially non-fluorescing. One approach is to additionally attach quenchers in close proximity to them. Another is based on the observation that when multiple fluorophores are attached to the capture system in close proximity to each other they tend to quench each other sufficiently well that the criterion described in the previous paragraph can be achieved without the need for quenchers. In this context of this patent, what constitutes 'close proximity' between fluorophores or between fluorophores and quenchers will depend on the particular fluorophores and quenchers used and possibly the structural characteristics of the single oligonucleotide. Consequently, it is intended that this term be construed with reference to the required outcome rather than any particular structural arrangement on the various elements of the capture system. However and for the purposes of providing exemplification only, it is pointed out that when adjacent fluorophores or adjacent fluorophores and quenchers are separated by a distance corresponding to the characteristic Förster distance (typically less than 5 nm) sufficient quenching will generally be achieved.

Suitably the capture system is labelled with up to 20, for example up to 10 and most preferably up to 5 fluorophores. To obtain maximum advantage, it is preferred that the capture system is labelled with at least 2 preferably at least 3 fluorophores. Consequently, ranges constructed from any permutation of these maxima and minima are specifically envisaged herein. If quenchers are employed, it is likewise preferred that the capture system is labelled with up to 20, preferably up to 10 and most preferably up to 5 of the same. Whilst it is envisaged that more than one type of fluorophore can be attached to the capture system, for example to give it a characteristic fingerprint, it is preferred that all the fluorophores employed in each capture system type are the same.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cy2, Cy3, Cy5 and Cy7. Specific examples include fluorophores derived from the following commonly used dyes: Alexa dyes, cyanine dyes, Atto Tec dyes, and rhodamine dyes. Examples also include: Atto 633 (ATTO-TEC GmbH), Texas Red, Atto 740 (ATTO-TEC GmbH), Rose Bengal, Alexa Fluor™ 750 $C_5$-maleimide (Invitrogen), Alexa Fluor™ 532 $C_2$-maleimide (Invitrogen) and Rhodamine Red $C_2$-maleimide and Rhodamine Green as well as phosphoramadite dyes such as Quasar 570. Alternatively a quantum dot or a near infra-red dye such as those supplied by LI-COR Biosciences can be employed. The fluorophore is typically attached to the second oligonucleotide via a nucleotide base using chemical methods known in the art.

Suitable quenchers are those which work by a Förster resonance energy transfer (FRET) mechanism. Examples of commercially available quenchers which can be used in association with the above mentioned-fluorophores include but are not limited to DDQ-1, Dabcyl, Eclipse, Iowa Black FQ and RQ, IR Dye-QC1, BHQ-0, BHQ-1, -2 and -3 and QSY-7 and -21.

Step (2) is suitably effected by contacting each single nucleotide base in the stream with the capture system, most preferably the multi-component capture system mentioned above, at a temperature in the range 30 to 80° C. in the presence of a two component enzyme system comprising a second polymerase and a ligase. In a preferred embodiment, the second polymerase is the same as that used in step (1) thereby avoiding the need to add this in the form of an extra component.

In step (3) of the method of the present invention, the detectable elements are released from the captured molecule in a detectable form by action of an exonuclease or the exonuclease activity of a polymerase. In doing so it is important that the fluorophores present in any of the unused sets of capture molecules are not at the same time released. In the case of the first class of capture system, this may be achieved for example by using a polymerase having 3'-5' exonuclease activity to degrade the captured molecule by virtue of its single-stranded overhang region. Alternatively, and especially in the case of the second class of capture systems, this may be achieved by incorporating into the capture system or the captured molecule at least one restriction enzyme recognition site preferably adjacent the region where the detectable elements are located or clustered. Such a restriction enzyme recognition site will typically comprise a specific sequence of from 2 to 8 nucleotide pairs. In a preferred embodiment of this approach, the restriction enzyme recognition site may be one created by binding of the single nucleotide base to the capture system.

Step (3) is also suitably carried out at a temperature in the range 30 to 80° C. Suitable examples of exonucleases or polymerases which can be used in this step include Phusion, Phusion HS, Dnase I (RNase-free), Exonuclease I or III (ex *E. coli*), Exonuclease T, Exonuclease V (RecBCD), Lambda Exonuclease, Micrococcal Nuclease, Mung Bean Nuclease, Nuclease BAL-31, RecJ$_f$, T5 Exonuclease and T7 Exonuclease. The net effect of step (3) is that the constituent nucleotides bases of the captured molecule will be liberated some of which will be labelled with the characteristic detectable element. Thus, when the captured molecule comprises multiple quenched fluorophores, this leads to a 'cascade' of liberated fluorophores which, by virtue of them becoming separated from each other and/or their associated quenchers, are now free to fluoresce in the normal way.

Thereafter, and in step (4), the detectable elements liberated from the degraded captured molecule are detected, the particular single nucleotide base identified and the sequence of nucleotide bases in the analyte recovered from the data stream associated with the detection. Methods of doing this are well-known in the art; for example fluorescence may be detected using a photodetector or an equivalent device tuned to the characteristic fluorescence wavelength(s) or wavelength envelope(s) of the various fluorophores. This in turn causes the photodetector to generate an electrical signal characteristic of a particular nucleotide base type which can be processed and thereafter analysed.

In a particularly preferred embodiment, the method of the present invention is carried out wholly or partially in microdroplets. Such a method may begin, for example, by inserting the single nucleotide bases generated in step (1) one-by-one into a corresponding stream of aqueous microdroplets in an immiscible carrier solvent such as a hydrocarbon or silicone oil to help preserve the ordering. Advantageously, this can be effected by directly creating the microdroplet downstream of the pyrophosphorolysis reaction zone; for example by causing the reaction medium to emerge from a microdroplet head of suitable dimensions into a flowing stream of the solvent. Alternatively, small aliquots of the reaction medium can be sequentially injected into a stream of pre-existing aqueous microdroplets suspended in the solvent. If this latter approach is adopted, each microdroplet may suitably contain the various components of the capture system and the enzymes and any other reagents (e.g. buffer) required to effect steps (2) and (3). Finally, the microdroplets created in the former embodiment can be caused to coalesce subsequently with a stream of such pre-exiting microdroplets to achieve a similar outcome. In this embodiment, step (4) then preferably involves interrogating each droplet in turn to identify the detectable elements liberated and hence the nature of the nucleotide base it contains.

To avoid the risk that a given microdroplet contains more than one single nucleotide base, it is preferred to release the single nucleotide bases in step (1) at a rate such that each filled microdroplet is separated by from 1 to 20 preferably 2 to 10 empty ones. Thereafter the stream of filled and unfilled microdroplets in the solvent is caused to flow along a flow path, suitably a microfluidic flow path, at a rate and in a manner such that the microdroplets are maintained in a discrete state and do not have the opportunity to coalesce with each other. Suitably the microdroplets employed have a diameter less than 100 microns, preferably less than 50 microns, more preferably less than 20 microns and even more preferably less than 15 microns. Most preferably of all their diameters are in the range 2 to 20 microns. In one embodiment, the microdroplet flow rate through the whole system is in the range 50 to 3000 droplets per second preferably 100 to 2000.

The method described above can be used to advantage in a sequencing device and such devices are envisaged as being within the scope of the invention.

The present invention will now be illustrated with reference to the following examples.

Preparation and Use of a Capture System

The following experiment illustrates the capture of a single nucleotide base and release of fluorophores using a capture system wherein the first oligonucleotide is j-shaped and the second is single-stranded.

A sample of a j-shaped oligonucleotide as described above is prepared by folding a 75 nucleotide base, single-stranded oligonucleotide having the following sequence:
gtaggtcctggcacagaaaaaggagGcagtgatgttccatgactgatttttttc-agtcatggaacatcact*g
wherein g, t, c, and a represent the conventional notation for the nucleotide bases of DNA and * represents the presence of a phosphorothioate linkage. Folding is carried out by heating an aqueous solution of this oligonucleotide to 95° C. and then cooling it slowly back to room temperature at a rate of 10 minutes per ° C. The j-shaped molecule so obtained comprises a residual single-stranded oligonucleotide region (gtaggtcctggcacagaaaaaggag) attached to a single nucleotide base which is the site of capture (capitalised in the above-mentioned sequence).

A corresponding single-stranded oligonucleotide is also prepared, having the following sequence:
^ctccTTXTTtctgtgccaga
wherein ^ represents a 5' phosphate group, a capitalised T represents a thymine base labelled with Alexa Fluor 488 dye via an azide linker, and an X represents a thymine base labelled with a BHQ-0 quencher.

Separate capture and nucleotide base mixtures are then prepared. The capture mixture has a composition corresponding to that derived from the following formulation:
2.5 ul 10× BufferII
5 ul 10× Taq Ligase buffer (NEB)
2.5 ul 100 nM of the j-shaped molecules mentioned above
5 ul 100 nM of the single-stranded oligonucleotide mentioned above
2 ul Thermostable Inorganic Pyrophosphatase (NEB)
5 ul Taq Ligase (NEB)
1 ul 25 mM MnSO4
water to 25 ul
whilst the nucleotide base mixture, whose composition is designed to mimic the material, obtained from the pyrophosphorolysis step, corresponds to that derived from the formulation:
2.5 ul 10 BufferII (supplied with Amplitaq; magnesium-free)
1.5 ul MgCl2 25 mM
2.5 ul 10 nM of deoxycytidine triphosphate (dCTP)
2 ul Amplitaq (5 U/ul)
2.5 ul 10 mM sodium pyrophosphate
water to 25 ul.

Capture of the dCTP is then effected by mixing together equal volumes of these two mixtures and incubating the resulting product at 50° C. This is typically complete in 30 minutes. At the end of this time a sample of the mixture (50 ul) is treated with 1 ul HotStart Phusion DNA polymerase (NEB) and activated at 98° C.×20 s so that exonucleolytic degradation of the completed capture molecules can occur. Degradation is typically complete within 30 minutes, and the released fluorophores can be detected by illuminating the sample at or close to the peak absorption wavelength (496 nm), and detecting the resulting fluorescence at the characteristic emission wavelength (519 nm).

Figure 2:
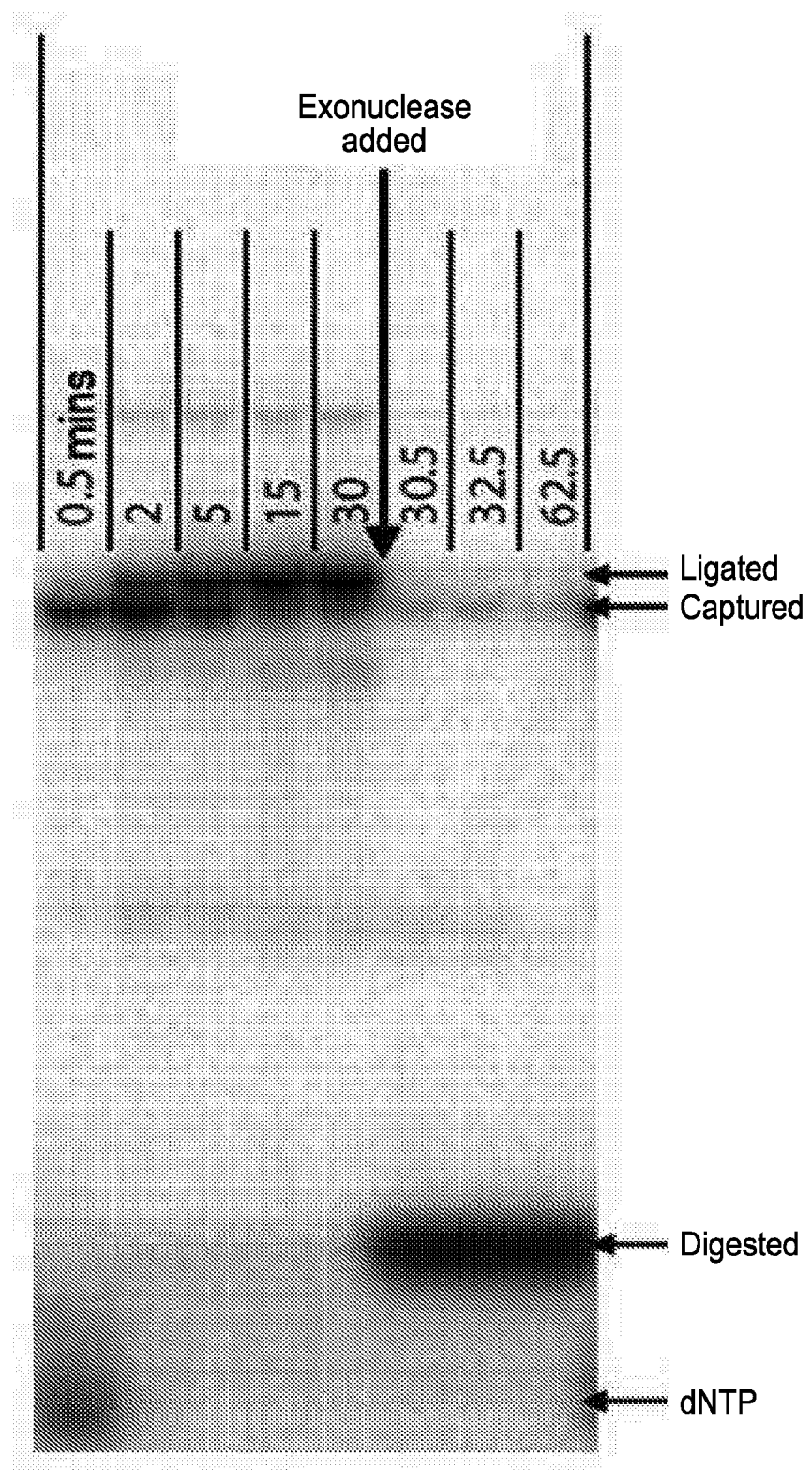
FIG. 2 shows the result of the capture of a single nucleotide base and release of fluorophores using a capture system over time using radio-labelled nucleotides and gel electrophoresis. The capture of the radio-labelled nucleotides onto the j-shaped oligonucleotide occurs within the first 2 minutes of the reaction, with ligation of the single stranded oligonucleotide occurring over the first 30 minutes. In this experiment the Phusion polymerase is added at time t=30 minutes, and it can be seen that the completed capture molecules are rapidly digested (in this case digestion occurs within 30 seconds of adding the polymerase).

FIG. 2 shows the result of this reaction over time using radio-labelled nucleotides and gel electrophoresis. The capture of the radio-labelled nucleotides onto the j-shaped oligonucleotide occurs within the first 2 minutes of the reaction, with ligation of the single stranded oligonucleotide occurring over the first 30 minutes. In this experiment the Phusion polymerase is added at time t=30 minutes, and it can be seen that the completed capture molecules are rapidly digested (in this case digestion occurs within 30 seconds of adding the polymerase).

Figure 3:
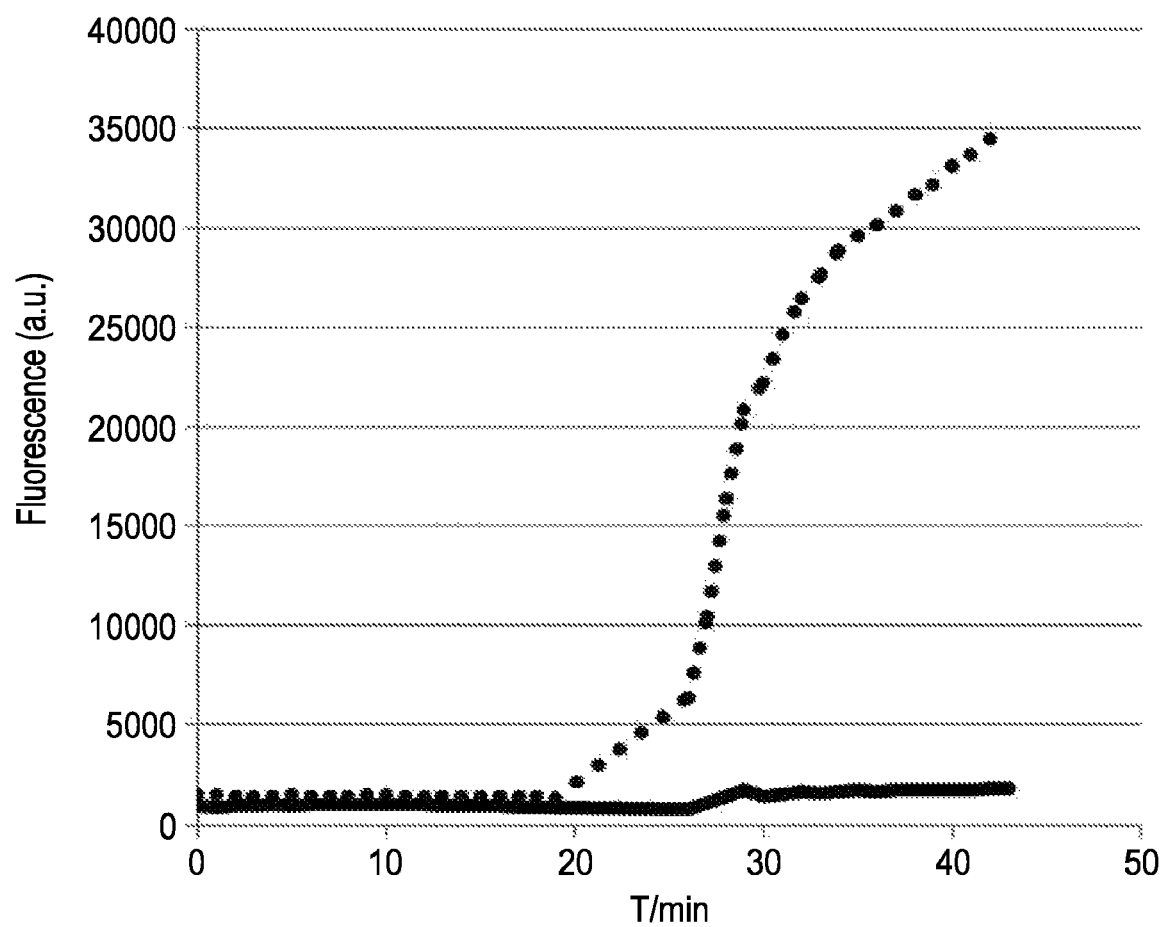
FIG. 3 shows the fluorescence measured as a function of time for the full reaction performed in the presence (broken line) or absence (solid line) of nucleotides. In this experiment the polymerase is heat-activated at time t=20 minutes. A significant increase in fluorescence is observed for the reaction performed in the presence of nucleotides, while little or no fluorescence increase is observed in their absence.

FIG. 3 shows the fluorescence measured as a function of time for the full reaction performed in the presence (broken line) or absence (solid line) of nucleotides. In this experiment the polymerase is heat-activated at time t=20 minutes. A significant increase in fluorescence is observed for the reaction performed in the presence of nucleotides, while little or no fluorescence increase is observed in their absence.

Droplet Microfluidic Method Using the Capture System

FIG. 1 illustrates a microfluidic sequencing device in which a stream of microdroplets at least some of which contain a single nucleotide base are made to undergo reaction with a capture system of the first class described above.

An aqueous medium 1 comprising a stream of discrete deoxyribonucleotide triphosphates obtained by the progressive pyrophosphorolysis of a 100 nucleotide base polynucleotide analyte derived from human DNA is caused to flow through a ten micron diameter microfluidic tube fabricated from PDMS polymer. The pyrophosphorolysis reaction itself is carried out by passing a stream of an aqueous, buffered (pH 8) reaction medium at 72° C., comprising Taq Pol and a 2 millimoles per litre concentration of each of sodium pyrophosphate and magnesium chloride, over a glass micro bead onto which the analyte has been previously attached by means of a succinyl bridge. The order of the single nucleotide bases in stream 1, which is downstream of the micro bead, corresponds to the sequence of the analyte. 1 emerges from a droplet head 2 into a first chamber 3 where it is contacted with one or more streams of immiscible light silicone oil 4. The velocities of these streams are chosen to avoid turbulent mixing and to create in 3 aqueous spherical droplets 5 suspended in the oil each having a diameter of approximately eight microns. Typically, the rate of pyrophosphorolysis and/or the rate of flow of 1 are adjusted so that between adjacent filled droplets there are 10 empty ones. A stream of 5 is then carried forward along a second microfluidic tube of the same diameter at a rate of 1000 droplets per second to a second chamber 6 into which a second stream of five micron aqueous spherical droplets 7 is also fed by means of a second droplet head 8. Droplets 5 and 7 are caused to coalesce in a sequential fashion to form enlarged aqueous droplets 9 approximately nine microns in diameter. Each of 7 contains pyrophosphatase to destroy any residual pyrophosphate anion present in each of 5.

A stream of 9 is then carried forward at the same rate via microfluidic tubing into a third chamber 10 where these droplets are contacted with a third stream of five micron aqueous spherical droplets 11 also fed thereto through a corresponding droplet head 12. The time taken for each of 9 to move between chambers 6 and 10 is c.2 minutes.

Droplets 9 and 11 are then caused to coalesce in 10 to produce droplets 13 (approximately ten microns in diameter). Each of 11 contains a mesophilic ligase and a capture system comprising four pairs of j-shaped first oligonucleotides and four corresponding second single-stranded oligonucleotides. In this example, each j-shaped first oligonucleotide is 60 nucleotide bases long and is prepared by folding a 60 nucleotide base single-stranded oligonucleotide precursor about the $45^{th}$ nucleotide base from the 5' end to generate a 3 nucleotide base single stranded loop, a 12 nucleotide base pair double-stranded region and a 33 nucleotide base single-stranded region. Each of these four first oligonucleotides has a different $33^{rd}$ base (measured from the single-stranded end) characteristic of the four characteristic nucleotide base types of DNA (i.e. A, T, G and C). The four different second oligonucleotides are each 28 nucleotide bases long and have sequences which are complimentary to that part of the single-stranded region defined by the $4^{th}$ and $32^{nd}$ nucleotide bases of their first oligonucleotide pair. The four different second oligonucleotide types are labelled respectively with the fluorophores Quasar 570, Fluorescein, Texas Red and Cy-5 (five fluorophores moieties per second oligonucleotide). In each case fluorescence is quenched by the inclusion of one quencher moiety on each second oligonucleotide (BHQ-2 for Quasar 570 and Texas Red, BHQ-0 for Fluorescein and BHQ-3 for cyanine-5).

A stream of 13 is next carried forward at the same rate via microfluidic tubing into a fourth chamber 14 where it is caused to coalesce with a fourth stream of five micron aqueous spherical droplets 15 also fed thereto through a droplet head 16. The time taken for each of 9 to move between the two chambers is 30 minutes in which time the single nucleotide base is captured by its capture system pair and the captured molecule formed. Each of 15 contains Phusion exonuclease to degrade the capture molecule and release the relevant fluorophores in detectable form. A stream of the coalesced microdroplets 17 is then taken forward to a container 18 in which their progress is tracked until they reach one of array of sites 19a where they are held 19b until such time as they are analysed.

After 2 hours each droplet held in the array is illuminated in turn and in the correct order with one or more high intensity light sources, for example one or more lasers emitting coherent light at the relevant frequencies of the fluorophores and the fluorescence so generated detected by a photodetector operating at those wavelengths characteristic of the four fluorophore types. From the information received the single nucleotide base is identified in each droplet and nil responses from empty droplets rejected. The results are then processed by a computer programmed to recreate the original nucleotide base sequence of the analyte. If so desired, multiple cycles of illumination and detection can be performed across the array of droplets at various intervals which can be averaged to improve the single to noise ratio and therefore the reliability of the results.

The invention claimed is:

1. A microfluidic device for sequencing a nucleic acid analyte comprising:
   (a) a nucleic acid pyrophosphorolysis zone including a bead-receiving location and a bead to which is attached the nucleic acid analyte;
   (b) at least one inlet connected to a source of an aqueous medium consisting essentially of a pyrophosphorolysing enzyme for introducing the aqueous medium into the pyrophosphorolysis zone upstream of the bead-receiving location via a first microfluidic pathway;
   (c) at least one first outlet for removing a stream of single nucleotides in the flowing aqueous medium downstream of the bead-receiving location via the first microfluidic pathway;
   (d) a microdroplet-generating chamber comprising a carrier solvent inlet, a first microdroplet head attached to the first outlet and a second outlet for removing a stream of microdroplets in the carrier solvent therefrom;
   (e) a second microfluidic pathway attached to the second outlet and provided with at least one microdroplet injector and/or at least one second microdroplet coalescence zone for introducing enzymes and biological probes into the first microdroplets;
   (f) a storage zone comprising locations at which the microdroplets issuing from the second microfluidic pathway are stored;
   (g) a light source for interrogating microdroplet locations;
   (h) a photodetector for detecting fluorescence at the microdroplet locations and generating an output data stream comprised of components characteristic of each single nucleotide in the stream of single nucleotides; and
   (i) a microprocessor programmed with a computer algorithm to recreate the original nucleotide base sequence of the nucleic acid analyte from the data stream.

2. The microfluidic device of claim 1, wherein the microdroplet head produces microdroplets having a finite diameter of less than 20 microns.

3. The microfluidic device of claim 1, wherein the second microfluidic pathway includes three microdroplet coalescence chambers arranged in series and each comprises a microdroplet head for introducing secondary microdroplets.

4. The microfluidic device of claim 1, wherein the light source is a laser.

5. The microfluidic device of claim 1 further comprising an aqueous medium containing a pyrophosphorolysing enzyme flowing through the nucleic acid pyrophosphorolysis zone.

6. The microfluidic device of claim 1, wherein the source of the aqueous medium consisting essentially of a pyrophosphorolysing enzyme is a reservoir.

7. A microfluidic device for sequencing a nucleic acid analyte comprising:
   (a) a nucleic acid pyrophosphorolysis zone including a bead-receiving location where pyrophosphorolysis of a polynucleotide attached to a bead is carried out;
   (b) at least one inlet connected to a source of an aqueous medium consisting essentially of a pyrophosphorolysing enzyme for introducing the aqueous medium into the pyrophosphorolysis zone upstream of the bead-receiving location via a first microfluidic pathway;
   (c) at least one first outlet for removing a stream of single nucleotides in the flowing aqueous medium from the bead-receiving location via the first microfluidic pathway;
   (d) a microdroplet-generating chamber comprising a carrier solvent inlet, a first microdroplet head attached to the first outlet and a second outlet for removing a stream of microdroplets in the carrier solvent therefrom;
   (e) a second microfluidic pathway attached to the second outlet and provided with at least one microdroplet injector and/or at least one second microdroplet coalescence zone for introducing enzymes and biological probes into the first microdroplets;
   (f) a storage zone comprising locations at which the microdroplets issuing from the second microfluidic pathway are stored;
   (g) a light source for interrogating microdroplet locations;
   (h) a photodetector for detecting fluorescence at the microdroplet locations and generating an output data stream comprised of components characteristic of each single nucleotide in the stream of single nucleotides; and
   (i) a microprocessor for analyzing the output data stream programmed with a computer algorithm to recreate the original nucleotide base sequence of the nucleic acid analyte from the data stream.

8. The microfluidic device of claim 7, wherein the source of the aqueous medium consisting essentially of a pyrophosphorolysing enzyme is a reservoir.

* * * * *

SEQUENCE LISTING

```
<160> NUMBER OF SEQ ID NOS: 3

<210> SEQ ID NO 1
<211> LENGTH: 75
<212> TYPE: DNA
<213> ORGANISM: Artificial Sequence
<220> FEATURE:
<223> OTHER INFORMATION: j-shaped oligonucleotide precursor
<220> FEATURE:
<221> NAME/KEY: misc_feature
<222> LOCATION: (74)..(75)
<223> OTHER INFORMATION: Phosphorothioate linkage

<400> SEQUENCE: 1
gtaggtcctg gcacagaaaa aaggaggcag tgatgttcca tgactgattt tttttttcagt      60 catggaacat cactg                                                        75

<210> SEQ ID NO 2
<211> LENGTH: 26
<212> TYPE: DNA
<213> ORGANISM: Artificial Sequence
<220> FEATURE:
<223> OTHER INFORMATION: Residual single-stranded oligonucleotide region
      of j-shaped oligonucleotide

<400> SEQUENCE: 2
gtaggtcctg gcacagaaaa aaggag                                            26

<210> SEQ ID NO 3
<211> LENGTH: 20
<212> TYPE: DNA
<213> ORGANISM: Artificial Sequence
<220> FEATURE:
<223> OTHER INFORMATION: single-stranded oligonucleotide
<220> FEATURE:
<221> NAME/KEY: misc_feature
<222> LOCATION: (5)..(6)
<223> OTHER INFORMATION: Thymine bases labelled with Alexa Fluor 488 via
      azide linker
<220> FEATURE:
<221> NAME/KEY: misc_feature
<222> LOCATION: (7)..(7)
<223> OTHER INFORMATION: Thymine base labelled with BHQ-0 quencher
<220> FEATURE:
<221> NAME/KEY: misc_feature
<222> LOCATION: (8)..(9)
<223> OTHER INFORMATION: Thymine bases labelled with Alexa Fluor 488 via
      azide linker

<400> SEQUENCE: 3
ctcctttttt ctgtgccaga                                                   20
```